(12) United States Patent
Funamura et al.

(10) Patent No.: US 8,317,758 B2
(45) Date of Patent: Nov. 27, 2012

(54) STOPCOCK VALVE

(75) Inventors: Shigeaki Funamura, Fukuroi (JP); Yosuke Sakai, Fukuroi (JP); Ichiro Kitani, Fukuroi (JP)

(73) Assignee: Covidien LP, Mansfield, MA (US)

( * ) Notice: Subject to any disclaimer, the term of this patent is extended or adjusted under 35 U.S.C. 154(b) by 438 days.

(21) Appl. No.: 12/027,773

(22) Filed: Feb. 7, 2008

(65) Prior Publication Data
US 2008/0319401 A1   Dec. 25, 2008

(30) Foreign Application Priority Data

Feb. 8, 2007   (JP) ................. 2007-028774

(51) Int. Cl.
*A61M 5/00* (2006.01)
(52) U.S. Cl. ............... 604/246; 137/625.46; 137/636.2
(58) Field of Classification Search ............ 604/246, 604/167.05, 167.01, 167.03, 248, 249, 256; 137/15.22, 247.21, 315.18, 449, 519.5, 533.11, 137/539, 625.46, 636.2, 625.41
See application file for complete search history.

(56) References Cited

U.S. PATENT DOCUMENTS

| | | | | |
|---|---|---|---|---|
| 1,478,688 A * | 12/1923 | Whidden | ............... | 137/625.16 |
| 1,614,437 A * | 1/1927 | Cochran | ............... | 137/625.41 |
| 3,747,641 A * | 7/1973 | Hare et al. | ............... | 137/625.41 |
| 4,043,359 A * | 8/1977 | Christo | ............... | 137/625.41 |
| 4,505,301 A * | 3/1985 | Yang | ............... | 137/625.41 |
| 5,478,318 A * | 12/1995 | Yoon | ............... | 604/167.05 |
| 5,664,603 A * | 9/1997 | Knapp | ............... | 137/625.4 |
| 5,740,836 A * | 4/1998 | Tang | ............... | 137/625.41 |
| 2006/0089603 A1 | 4/2006 | Truitt et al. | | |

FOREIGN PATENT DOCUMENTS

JP    S62-172962    7/1987

OTHER PUBLICATIONS

Extended European Search Report issued in Application 08101417.7-1257, dated May 30, 2008, 6 pages.
Canadian Examination Report from Application No. 2619205 mailed Feb. 28, 2012.

\* cited by examiner

*Primary Examiner* — Kevin C Sirmons
*Assistant Examiner* — Kami A Bosworth
(74) *Attorney, Agent, or Firm* — Lisa E. Winsor, Esq.

(57) ABSTRACT

A medical stopcock which allows easier switching operation of plural branch-tubes. The main body of the stopcock comprises a chamber part with a nearly spherical inner surface, and an upstream branch-tube, a downstream branch-tube and a merge-branch-tube all extending from the chamber part. A valve body of the stopcock comprises a nearly spherical valve main body and a rod-shaped operating part with a guide hole linking the inner surface of the chamber part to the outside. In operation, the rod-shaped operating part is moved along the guide hole through the use of the horizontal flow passages and the vertical flow passage to allow the predetermined branch-tubes out of the upstream branch-tube, the downstream branch-tube and the merge-branch-tube to communicate with one another or to shut-off the communication.

7 Claims, 5 Drawing Sheets

STOPCOCK VALVE

FIELD OF THE INVENTION

The present invention relates to a medical stopcock comprising plural branch-tubes connected to the plural infusion tubes and the likes used for medical purposes and capable of switching the communication and shut-off statuses of each branch-tube.

BACKGROUND OF THE INVENTION

Traditionally, plural infusion tubes are used to supply fluids such as drug solutions into a patient's body, in cases like this, medical stopcocks are used to allow the solutions to communicate between each infusion tub or shut-off the communication. Among the foregoing medical stopcocks, there exist medical stopcocks capable of allowing an operator to open or shut-off the communication between each branch-tube and the chamber part by moving the operating part in the axial direction of the chamber part, wherein the chamber part has a cylindrical shape (for example, see Unexamined Patent Publication S62-172962). The medical stopcock disclosed in this prior art is formed in such a manner that 2 branch-tubes are provided interposing the peripheral surface of an approximately cylindrically shaped chamber part, and the valve body in the axial direction in the chamber part can be rotated to open and close the communication between the 2 branch-tubes.

However, this medical stopcock is provided with only 2 branch-tubes, and only capable of simply allowing one to open or shut-off the communication between the 2 branch-tubes. Hence, this medical stopcock cannot be connected to plural lines of infusion tubes and analogs used for medical purposes to switch the communication and shut-off statuses of each infusion tube. Moreover, in order to allow the 2 branch-tubes to communicate with one another or shut-off the communication with one another, the rotational manipulation of the valve body must be performed, posing a difficulty to operate. Consequently, the medical stopcock comprising 3 branch-tubes, capable of switching the flow passage by performing the rotational manipulation of the cock in the axial direction of the valve body has also been developed. However, even in such a medical stopcock, during the manipulation, the main body of the medical stopcock needs to be held by one hand, and the cock needs to be manipulated by the other hand, and therefore it is difficult to operate.

The present invention is made in consideration of the foregoing situations, and the purpose is to provide a medical stopcock allowing an easy switching operation of the flow passages of plural branch-tubes.

SUMMARY OF THE INVENTION

In one aspect, the present invention is directed to a medical stopcock comprising a medical stopcock main body including a chamber part, plural branch-tubes, a valve main body, and a rod-shaped operating part. The chamber part has an open space part the inner surface of which is formed approximately spherically and a guide hole located at a predetermined position of said inner surface through to the outside. Each of the plural branch-tubes has a flow passage spaced from the outer peripheral surface of said chamber part and extending outward respectively to communicate with inside said chamber part. The valve main body comprises an approximately spherical body installed in the said chamber part. The spherical body is provided with flow passages formed at a predetermined position thereon and capable of allowing predetermined branch-tubes out of said plural branch-tubes to communicate with one another through the use of said flow passages or of shutting-off the communication by rotationally moving along the inner surface of said chamber part. A rod-shaped operating part allowing the flow passages of said valve main body to communicate with predetermined branch-tubes out of said plural branch-tubes, or shutting-off the communication by passing through said guide hole from the outer peripheral surface of said valve main body and extending outward and by moving along said guide hole.

DESCRIPTION OF FIGURE NOTATIONS

10 . . . Medical stopcock main body,
11,31 . . . Chamber parts,
11a . . . Open space part,
12,32 . . . Upstream branch-tubes,
12a,13a,14a, and
34a . . . Flow passages,
13,33 . . . Downstream branch-tubes,
14,34 . . . Merge-branch-tubes,
15 . . . Guide hole,
15a . . . Horizontal guide hole,
15b . . . Vertical guide hole,
20 . . . Valve disc,
21,35 . . . Valve main bodies,
22 . . . Rod-shaped operating part,
23 . . . Horizontal flow passages,
24,38 . . . Vertical flow passages, A,B . . . Medical stopcock.

DETAILED DESCRIPTION OF THE INVENTION

Figure 1:
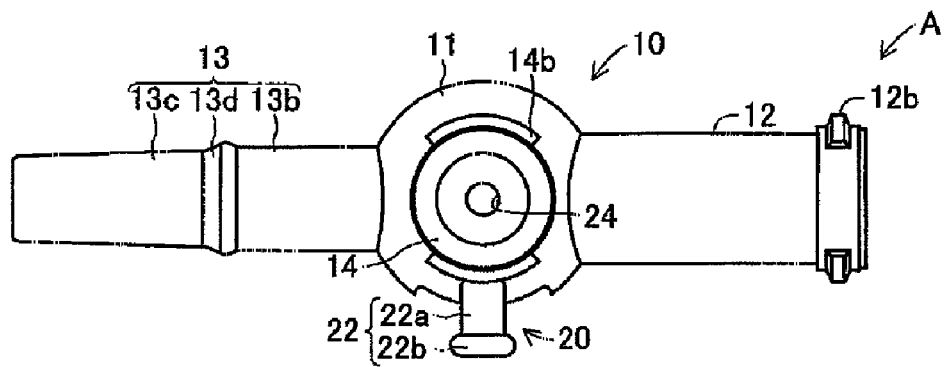
FIG. 1 is a plane view showing a medical stopcock according to the first embodiment of the present invention.
Figure 2:
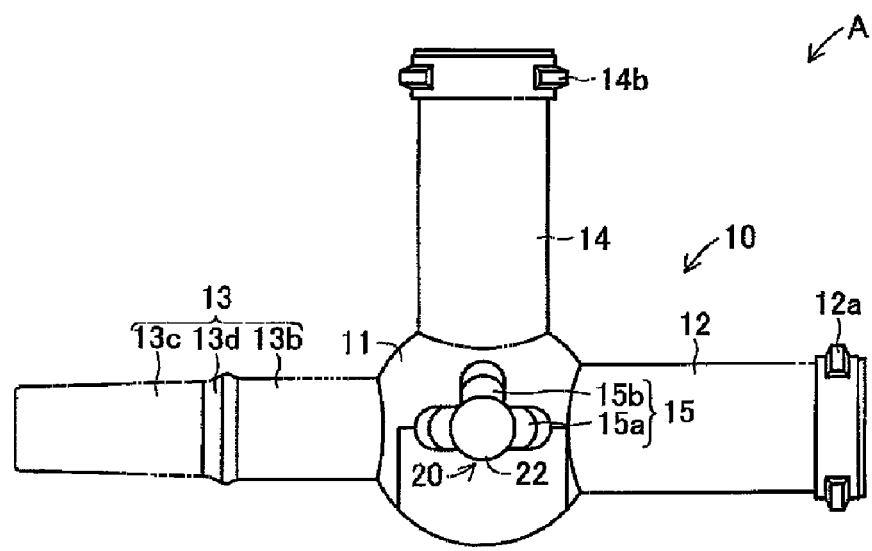
FIG. 2 is a side view showing a medical stopcock.
Figure 3:
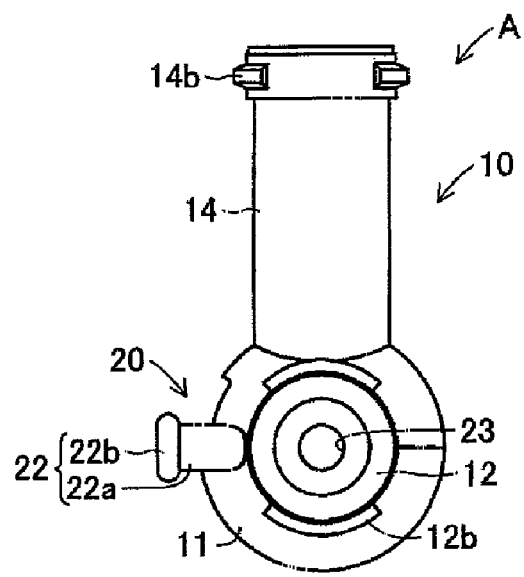
FIG. 3 is a back view showing a medical stopcock.

The First Embodiment. A medical stopcock according to the first embodiment of the present invention will be described in detail with reference to drawings. FIG. 1 or FIG. 3 shows a medical stopcock-A according to the first embodiment. This medical stopcock-A is comprised of a medical stopcock main body 10 and a valve body 20 installed inside the medical stopcock main body 10. The medical stopcock main body 10 comprises an approximately spherical chamber part 11; an upstream branch-tube 12 and a downstream branch-tube 13 as a pair of horizontal branch-tubes connected to both front and rear sides (right and left sides in FIG. 1 and FIG. 2; hereinafter, the direction located in the upstream of the drug solution flow is described as the "rear side" and the direction located in the downstream is described as the "front side") in the outer peripheral surface of the chamber part 11 so as to be extending in the horizontal direction along coaxially; and a merge-branch-tube 14 as the vertical branch-tube of the invention formed at the upper part in the outer peripheral surface of the chamber part 11.

Figure 4:
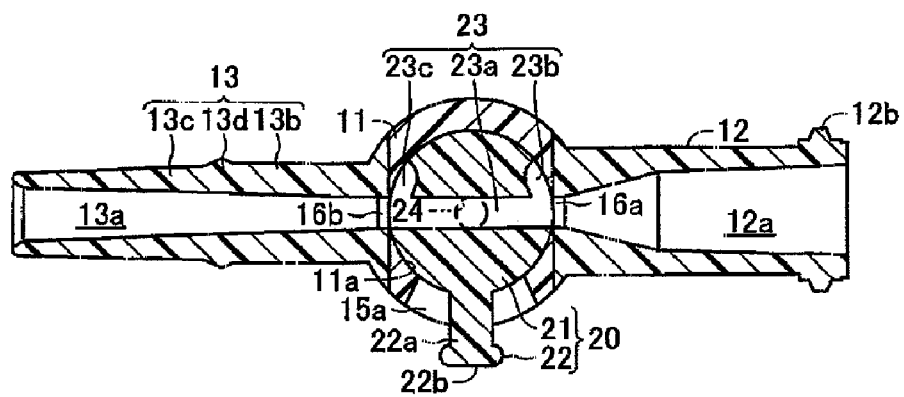
FIG. 4 is a transverse cross-section view of FIG. 1.
Figure 6:
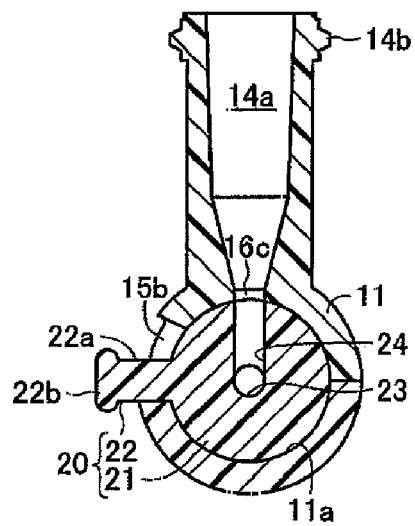
FIG. 6 is a longitudinal cross-section view FIG. 3.

More specifically, the upstream branch-tube 12, the downstream branch-tube 13 and the merge-branch-tube 14 are provided on the outer peripheral surface of the chamber part 11, are circumferentially spaced at 90-degrees, and the merge-branch-tube 14 is extending upward so as to be perpendicularly intersecting with the upstream branch-tube 12 and the downstream branch-tube 13 extending in the horizontal direction. The chamber part 11 is formed in an approximately spherical shape, inside of which, as shown in FIG. 4 or FIG. 6, the open space part 11a the inner peripheral surface of which is formed approximately spherically. Moreover, a horizontal guide hole 15a extending anteroposteriorly is formed at the center in the vertical direction on the side surface (the surface shown in FIG. 2) of the chamber part 11 passing through inside the chamber part 11 outward, and a vertical guide hole 15b passing through inside the chamber part 11 outward is extending from the center of the cross direction of the horizontal guide hole 15a upward.

In addition, communication holes 16a, 16b and 16c are formed at positions opposing to the upstream branch-tube 12, the downstream branch-tube 13 and the merge-branch-tube 14 respectively in the chamber part 11. And, the upstream branch-tube 12 is provided at a position corresponding to a communication hole 16a in the outer peripheral surface of the chamber part 11, and through the use of the communication hole 16a, the open space part 11a in the chamber part 11 is communicated with a flow passage 12a formed inside the upstream branch-tube 12. Moreover, the downstream branch-tube 13 is provided at a position corresponding to a communication hole 16b in the outer peripheral surface of the chamber part 11, and through the use of the communication hole 16b, the open space part 11a inside the chamber part 11 is communicated with a flow passage 13a formed inside the downstream branch-tube 13.

Further, a merge-branch-tube 14 is provided at a position corresponding to a communication hole 16c in the outer peripheral surface of the chamber part 11, through the use of the communication hole 16c, the open space part 11a inside the chamber part 11 is communicated with a flow passage 14a formed inside the merge-branch-tube 14. Moreover, the upstream branch-tube 12 is integrally formed with the chamber part 11, the flow passage 12a formed inside thereof formed in a tapered shape with the diameter of the rear end opening side being larger and the diameter of the chamber part 11 side being smaller.

Figure 5:
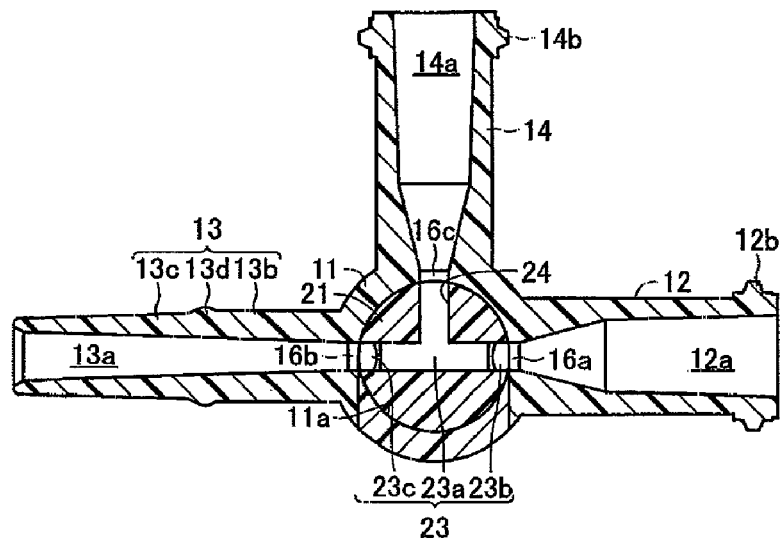
FIG. 5 is a longitudinal cross-section view of FIG. 2.

Specifically, flow passage 12a is formed in a somewhat steep tapered shape with the diameter of the communication hole 16a side portion being larger toward the communication hole 16a and being smaller away form the communication hole 16a. Moreover, the upstream portion (the right side portion in FIG. 4 and FIG. 5) of the flow passage 12a is formed in a gradual tapered shape with the diameter increasing gradually toward the opening of the upstream branch-tube 12. Further, a connecting screw part 12b is formed at the outer peripheral surface of the opening of the upstream branch-tube 12.

The downstream branch-tube 13 is integrally formed with the chamber part 11 and is comprised of a base part 13b located at the chamber part 11 side and a male luer part 13c which is positioned at the tip side and formed thinner than a base part 13b. Moreover, the male luer part 13c is formed in a tapered-off shape with the tip side being thinner than the base part 13b side, gradually tapered-off to the point. And, a protrusion part 13d is formed along the circumference at the boundary part between the base part 13b and the male luer part 13c in the outer peripheral surface of the downstream branch-tube 13.

The merge-branch-tube 14 formed at the upside of the chamber part 11 is formed in a cylindrical shape with the size and the axial length being approximately the same degree as the upstream branch-tube 12. The flow passage 14a formed inside this merge-branch-tube 14 is formed in a somewhat steep tapered shape with the diameter in the communication hole 16c side position being smaller toward the communication hole 16c and larger away from the communication hole 16c. And, the upstream position (the top side portion in FIG. 5) of the flow passage 14a is formed in a gradually tapered shape with the diameter being gradually larger toward the openings of the merge-branch-tube 14. Further, a connecting screw part 14b is formed at the outer peripheral surface of the opening of the merge-branch-tube 14.

The valve body 20 is comprised of the valve main body 21 formed in an approximately spherical shape installed at the open space part 11a of the chamber part 11, and the rod-shaped operating part 22 passing through the guide hole 15 comprised of the horizontal guide hole 15a and the vertical guide hole 15b extending from the valve main body 21 to the outside. The valve main body 21 is installed in the chamber part 11 with the outer surface being slidingly contacted with the inner surface of the chamber part 11, and is rotatable around the center of spherical shape in every direction to the chamber part 11, the rotation range of which however is restricted by the engagement between a rod-shaped operating part 22 and the guide hole 15.

Further, as shown in FIG. 4 or FIG. 6, the horizontal flow passages 23 passing through the valve main body 21 and extending anteroposteriorly, and the vertical flow passages 24 passing through from the center of the cross direction of the horizontal flow passages 23 to the upper part of the valve main body 21 are formed inside the valve main body 21. The horizontal flow passages 23 are constituted by forming circular arc shaped expanded (wide-angle) open space parts 23b, 23c extending to one of side part sides (the upper part side in FIG. 4) respectively, at both the front and rear ends of thin cylindrically shaped open space part 23a extending anteroposteriorly. The expanded (wide-angle) open space parts 23b, 23c are, with the respective widths in the vertical direction being the same with the width of the open space part 23a, extending face-to-face so as to be along the inner surface of the chamber part 11.

Additionally, the width in the horizontal direction of the expanded (wide-angle) open space part 23b is determined to be approximately 2 times of the diameter of the communication hole 16a, and the width in the horizontal direction of expanded (wide-angle) open space part 23c is determined to be approximately 2 times of the diameter of the communication hole 16b. Consequently, as shown in FIG. 4, when the rod-shaped operating part 22 is positioned at the center of the horizontal guide hole 15a, the open space part 23a side position of the expanded (wide-angle) open space part 23b and the communication hole 16a are opposed, and the expanded (wide-angle) open space part 23c and the communication hole 16b are communicated. Thereby, the flow passage 12a of the upstream branch-tube 12 and the flow passage 13a of the downstream branch-tube 13 are communicated through the use of the horizontal flow passages 23 of the valve main body 21.

Figure 7:
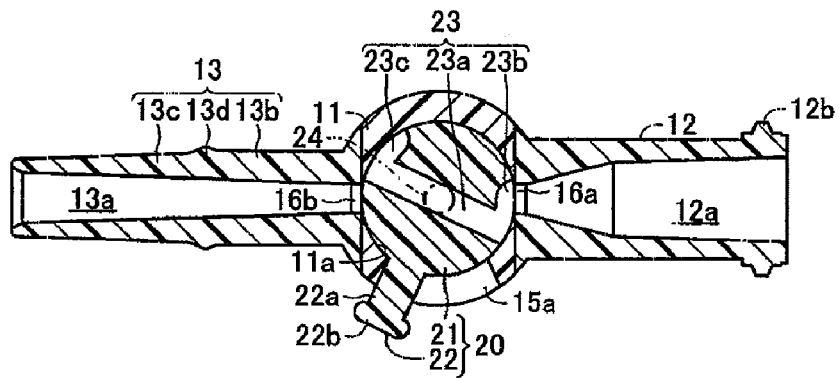
FIG. 7 is a transverse cross-section view showing the condition in which an upstream branch-tube and a merge-branch-tube are made to communicate.
Figure 8:
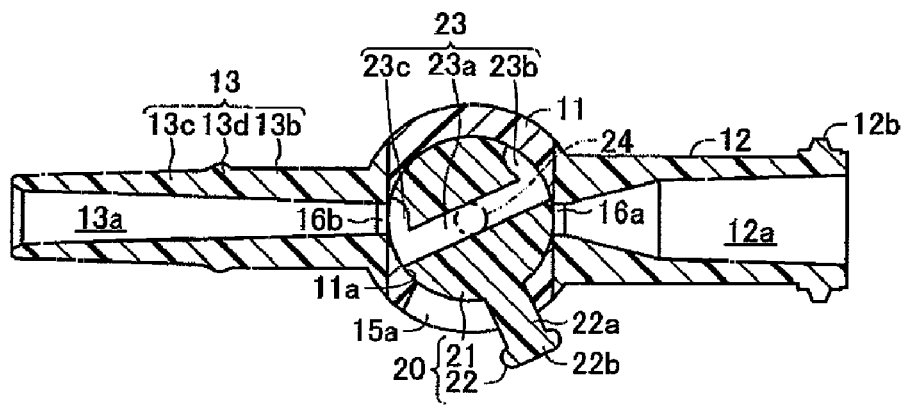
FIG. 8 is a transverse cross-section view showing the condition in which a downstream branch-tube and a merge-branch-tube are made to communicate.

Moreover, as shown in FIG. 7, when the rod-shaped operating part 22 is positioned at the front end side of the horizontal guide hole 15a, the tip side position of the expanded (wide-angle) open space part 23b and the communication hole 16a are opposed, and the expanded (wide-angle) open space part 23c is obstructed to the inner surface of the chamber part 11, and the communication holes 16b is obstructed to the outer surface of the valve main body 21. Consequently, the flow passage 12a of the upstream branch-tube 12 and the horizontal flow passages 23 of the valve main body 21 are communicated. However, the communication status of the horizontal flow passages 23 of the valve main body 21 and the flow passage 13a of the downstream branch-tube 13 becomes "shut-off". In addition, as shown in FIG. 8, when the rod-shaped operating part 22 is positioned at rear end side of the horizontal guide hole 15a, the expanded (wide-angle) open space part 23b is obstructed to the inner surface of the chamber part 11, and the communication hole 16a is obstructed to the outer surface of the valve main body 21.

Moreover, the tip side position of the expanded (wide-angle) open space part 23c is opposed to the communication holes 16b to communicate. Consequently, the communication status of the flow passage 12a of the upstream branch-tube 12 and the horizontal flow passages 23 of the valve main body 21 are shut-off, and the horizontal flow passages 23 of the valve main body 21 and the flow passage 13a of the downstream branch-tube 13 are communicated. A vertical flow passage 24 is comprised of a thin cylindrically shaped open space part extending in the vertical (up/down) direction, the diameter of which is determined to be the same as the diameter of the open space part 23a and the diameter of the communication hole 16c. Moreover, the upper end opening of a vertical flow passage 24 is formed at a position to be communicated with the communication hole 16c when the rod-shaped operating part 22 is positioned at the center of the horizontal guide hole 15a.

Figure 9:
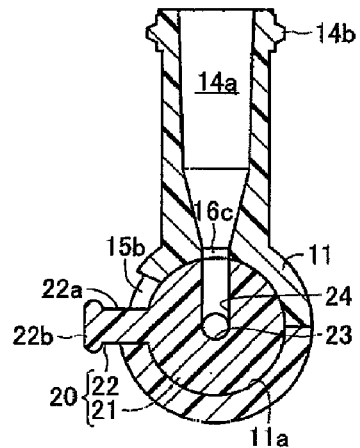
FIG. 9 is a longitudinal cross-section view showing the condition in which horizontal flow passages and a merge-branch-tube are made to communicate.
Figure 10:
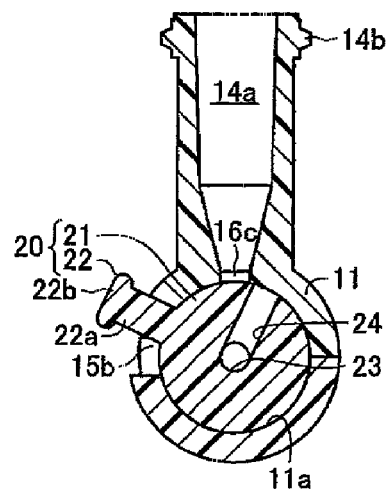
FIG. 10 is a longitudinal cross-section view showing the condition in which the communication between a horizontal flow passage and a merge-branch-tube is shut-off.

Hence, in the condition shown in FIG. 4 and FIG. 9, the upstream branch-tube 12 and the downstream branch-tube 13 are communicated through the use of the horizontal flow passages 23, and the flow passage 14a of the merge-branch-tube 14 and the horizontal flow passages 23 are communicated through the use of the vertical flow passage 24. Consequently, all of the upstream branch-tube 12, the downstream branch-tube 13 and the merge-branch-tube 14 are communicated through the use of the horizontal flow passages 23 of the valve main body 21 and the vertical flow passage 24. And, as shown in FIG. 10, when the rod-shaped operating part 22 is made to move to the upper end side of the vertical guide hole 15b, the upper end opening of the vertical flow passage 24 is obstructed to the inner surface of the chamber part 11, and the communication hole 16c is obstructed to the outer surface of the valve main body 21. Consequently, the communication status of the flow passage 14a of the merge-branch-tube 14 and the vertical flow passage 24 of the valve main body 21 becomes "shut-off".

In this case, the valve main body 21 simply rotates in the axial direction around the central axis of the open space part 23a, and therefore the communication status of the upstream branch-tube 12 and the downstream branch-tube 13 through the use of the horizontal flow passages 23 does not change.

Incidentally, in FIG. 4, FIG. 7 and FIG. 8, the vertical flow passage 24 is positioned at the upside of the position shown in the figures. Moreover, the rod-shaped operating part 22 is comprised of a cylindrically shaped connection part 22a extending from the outer surface of the valve main body 21 to the outside, and an approximately disc-shaped grip part 22b formed at the tip part of the connection part 22a. And, by manipulating the grip part 22b with fingers to move the rod-shaped operating part 22 along the guide hole 15, as mentioned above, the communication status of the upstream branch-tube 12, the downstream branch-tube 13 and the merge-branch-tube 14 can be switched between communication and shut-off statuses.

In this configuration, in the event that predetermined drug solutions are supplied into a patient (not shown) body, the male luer parts (not shown) provided at the tip parts of infusion tubes extending from containers and the likes containing drug solutions to be supplied to the patient, are connected to the upstream branch-tube 12 and the merge-branch-tube 14 respectively. Moreover, the downstream branch-tube 13 is connected to the rear end parts of infusion tubes (not shown) to which indwelling needles for puncturing and being indwelled within the patient are connected. And, with the indwelling needles punctured the patient's body and indwelled within, the rod-shaped operating part 22 is manipulated, for example, is moved to the upper end side of the vertical guide hole 15b to pump the drug solutions in the containers and the likes connected to the upstream branch-tube 12 side into the patient, thereby drug solutions can be supplied into the patient from the upstream branch-tube 12 through the downstream branch-tube 13.

Moreover, in addition to drug solutions supplied from the upstream branch-tube 12 side, in the event that the other drug solutions and the likes are supplied into the patient, the other drug solutions and the likes are supplied into the vertical flow passage 24 through the use of the merge-branch-tube 14. In this case, with the rod-shaped operating part 22 being moved to the lower end part (the center of the horizontal guide hole 15a) of the vertical guide hole 15b, and the drug solutions in the container and the likes connected to the merge-branch-tube 14 are pumped into the merge-branch-tube 14 side. Thereby, the drug solutions supplied from the upstream branch-tube 12 side and the drug solutions supplied from the merge-branch-tube 14 side are mixed in the horizontal flow passages 23 and supplied into the patient's body.

Moreover, from the condition thereof, the rod-shaped operating part 22 is moved to the rear end side of the horizontal guide hole 15a to achieve the condition in FIG. 8, thereby, the supply of the drug solutions from the upstream branch-tube 12 side can be stopped to supply only the drug solutions from the merge-branch-tube 14 side into the patient's body. In addition, the rod-shaped operating part 22 is moved to the front end side of the horizontal guide hole 15a, making the condition the same in FIG. 7, thereby, the supply of the drug solutions into the downstream branch-tube 13 side can be stopped and at the same time, the drug solutions from the merge-branch-tube 14 side can be channeled off to the upstream branch-tube 12 side, and the drug solutions of the upstream branch-tube 12 side and the drug solutions from the merge-branch-tube 14 can be mixed at the upstream branch-tube 12 side. And, the mixed drug solutions can be again supplied into the patient's body by allowing the downstream branch-tube 13 to communicate with the horizontal flow passages 23.

Thus, in a medical stopcock-A according to an embodiment of the current invention, the open space part, the inner surface of which is formed approximately spherically 11a is provided inside the chamber part 11, and the valve main body in an approximately spherical shape 21 is installed in this open space part 11a. Moreover, the valve main body 21 is rotatably installed with the outer surface being slidingly contacted with the inner surface of the chamber part 11, and in the inside thereof, the horizontal flow passages 23 capable of allowing the upstream branch-tube 12 to communicate with the downstream branch-tube 13 or shutting-off the communication, and the vertical flow passages 24 capable of allowing the communication between the merge-branch-tube 14 and the horizontal flow passages 23 to open or shut-off.

Moreover, in the chamber part 11, the guide hole 15 consisting of the horizontal guide hole 15a and the vertical guide hole 15b is formed, and the rod-shaped operating part 22 extending from the valve main body 21 passing through the guide hole 15 to the outside can be moved along the guide hole 15, thereby the communication between the upstream branch-tube 12 and the downstream branch-tube 13 can be opened or shut-off, as well as the communication between the merge-branch-tube 14 and the horizontal flow passages 23 can be opened or shut-off. Consequently, the switching operation between the upstream branch-tube 12, the downstream branch-tube 13 or the merge-branch-tube 14 can be performed by simply moving the rod-shaped operating part 22 along the guide hole 15, allowing one hand operation.

Moreover, when the rod-shaped operating part 22 positioned at a location where the horizontal guide hole 15a and the vertical guide hole 15b are intersected with one another, all of the upstream branch-tube 12, the downstream branch-tube 13 and the merge-branch-tube 14 can be communicated, and when the rod-shaped operating part 22 is moved backward/forward or upward from the position, either one of branch-tubes is shut-off. In this case, it is formed in such a manner that the rod-shaped operating part 22 faces in the direction of the branch-tube to be shut-off, therefore, the communication statuses of the upstream branch-tube 12, the downstream branch-tube 13 and the merge-branch-tube 14 can be identified according to the facing direction of the rod-shaped operating part 22, Consequently, an operational error can be prevented.

Figure 11:
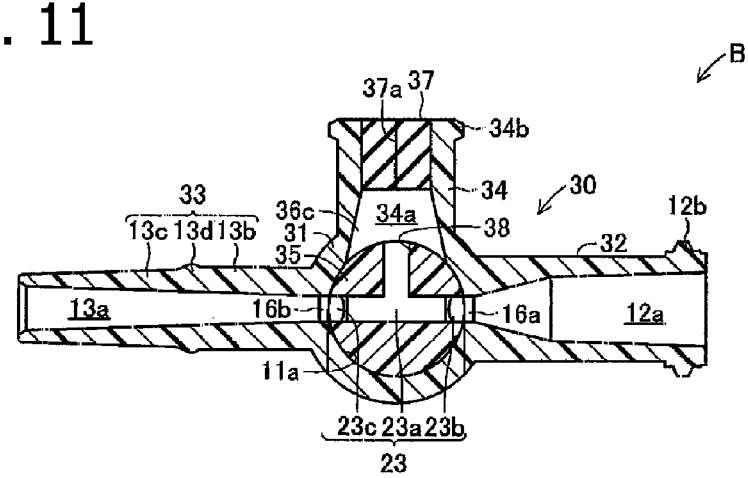
FIG. 11 is a longitudinal cross-section view showing the condition in which an upstream branch-tube and a downstream branch-tube of a medical stopcock according to the second embodiment of the present invention are made to communicate.

The Second Embodiment. FIG. 11 shows a medical stopcock-B according to the second embodiment of the present invention. In this medical stopcock-B, the diameter of a communication holes 36c formed at the upper part of the chamber part 31 is made larger, and the peripheral surface is formed in a tapered shape with the chamber part 31 side being made larger but smaller toward the upper part side. And, a merge-branch-tube 34 formed at the upside of the chamber part 31 is formed in a cylindrical shape with the diameter larger and the axial length shorter than the aforementioned merge-branch-tube 14. Moreover, the peripheral surface of flow passage 34a formed inside this merge-branch-tube 34 is formed with tapered surface continuous to the tapered surface of the communication holes 36c, with the diameter being larger toward the communication holes 36c and smaller away from the communication holes 36c.

Further, the upside portion of the flow passage 34a is comprised of the opening with the diameter being the same from the upper end of the flow passage 34a to the outside. Moreover, the connecting screw part 34b is formed at the outer peripheral surface of the upper end opening of the merge-branch-tube 34. Additionally, a rubber plug 37 consisting of naturally occurring rubber or synthetic rubber is attached at the upper end inside the merge-branch-tube 34. This rubber plug 37 is provided with a slit 37a vertically passing through between the inner side of the chamber part 31 and the outer side of the merge-branch-tube 34, and this slit 37a is obstructed by the elasticity of the rubber plug 37 when the merge-branch-tube 34 is not in use.

When the merge-branch-tube 34 is used, for example, the male luer part of the syringe and the likes (not shown) can be inserted into the slit 37a of the rubber plug 37 to allow the syringe to communicate with a flow passage 34a. Moreover, although not illustrated, the guide hole formed at the chamber part 31 is comprised of the horizontal guide hole only but not the vertical guide hole. Consequently, by the rotation of the valve main body 35, the communication between an upstream branch-tube 32 and a downstream branch-tube 33 can be opened or shut-off, and a vertical flow passage 38 formed at the valve main body 35 is constantly in communication with the flow passage 34a. The constitutions of this medical stopcock-B other than the positions described above are the same as the aforementioned medical stopcock-A. Thus, the identical notations are assigned to the identical parts and the detailed descriptions are omitted.

Because of the configurations as described above, with the male luer part of the syringe being inserted into the slit 37a of the rubber plug 37, the rod-shaped operating part 22 can be moved to the center of the horizontal guide hole, thereby the syringe can be made to communicate with the upstream branch-tube 32 and the downstream branch-tube 33. Thereby, 2 kinds of drug solutions and the likes can be supplied into the patient's body. Moreover, while maintaining the condition thereof, the syringe can be removed to obstruct the rubber plug 37, thereby only the upstream branch-tube 32 and the downstream branch-tube 33 are allowed to be communicated. In addition, with the male luer part of the syringe being inserted into the slit 37a of the rubber plug 37, the communication between the upstream branch-tube 32 and the horizontal flow passages 23 can be shut-off, thereby only the syringe and the downstream branch-tube 33 are allowed to be communicated.

Thus, only 1 kind of drug solution and the like can be supplied into the patient's body. Moreover, with the male luer part of the syringe being inserted into the slit 37a of the rubber plug 37, the communication between the horizontal flow passages 23 and the downstream branch-tube 33 can be shut-off, thereby only the syringe and the upstream branch-tube 32 are allowed to be communicated. In addition, while maintaining the condition thereof, the syringe can be removed, thereby all the flow passages of the upstream branch-tube 32, the downstream branch-tube 33 and the merge-branch-tube 34 can be obstructed. The effects of this medical stopcock-B other than the positions described above are the same as the aforementioned medical stopcock-A.

Moreover, the medical stopcock according to the present invention is not limited to the aforementioned embodiments and, in other embodiments of the invention, may be arbitrarily modified and implemented accordingly within the scope of the invention. For example, in each of the aforementioned embodiments, the horizontal flow passages 23 and the vertical flow passage 24 are provided inside the valve main bodies 21 and 35. However, in another embodiment of the invention, this horizontal flow passages and the vertical flow passage may also be formed along the surface of the valve main body. Moreover, in each of the aforementioned embodiments, plural branch-tubes are comprised of 3 branch-tubes: the upstream branch-tube 12 (32), the downstream branch-tube 13 (33) and the merge-branch-tube 14 (34); however, in other embodiments of the invention, these tubes may also be comprised of 2 branch-tubes.

In addition, in the aforementioned second embodiment, the rubber plug 37 is provided with the slit 37a, and the male luer part is inserted into the slit 37a to allow the syringe to communicate with the merge-branch-tube 34. However, in lieu of the syringe, an insertion part of a connector, or needles such as an injection needle or a dull needle may also be inserted into the rubber plug 37. Incidentally, in the event that an injection needle is inserted, the slit 37a provided for the rubber plug 37 is no longer required. In addition, in other embodiments of the invention, the configurations of any other portions forming the medical stopcock other than described above may also be arbitrarily modified and implemented accordingly.

In an aspect of the medical stopcock of the present invention configured as described above, the open space part, the inner surface of which is formed approximately spherically is provided inside the medical stopcock main body provided with the plural branch-tubes, and the valve main body in an approximately spherical shape comprising the flow passages capable of allowing the predetermined branch-tubes out of the plural branch-tubes to communicate with one another or shut-off the communication one another is installed in this open space part. Furthermore, the medical stopcock is formed in such a manner that the valve main body is rotated in the chamber part by moving the rod-shaped operating part, which is passing through the guide hole formed at the valve main body to the chamber part extending to outside, along the guide hole allowing the predetermined branch-tubes out of the plural branch-tubes to communicate with one another or shut-off the communication through the use of the flow passages of the valve main body.

Consequently, the switching operation between each branch-tube can be performed simply by moving the rod-shaped operating part along the guide hole, and whereas the movement of the rod-shaped operating part is a rotation around the valve main body as a pivot point, one hand operation can be performed. More specifically, the rod-shaped operating part may be operated with the thumb of a hand holding the chamber part. Moreover, the predetermined position of the valve main body on which the flow passages are formed may be either the inside or the surface of the valve main body, and the flow passages may be comprised of holes passing through the valve main body or grooves formed along the surface of the valve main body In addition, the "approximately spherical surface" of the inner surface of the chamber part and the "approximately spherical body" of the valve main body means that they are, in their entirety, a spherical surface and a spherical body respectively, however are not a perfect spherical surface and a perfect spherical body due to the hole and the flow passages provided thereon, and the valve main body is slidingly contacting with the inner surface of the chamber part and is rotatable.

Moreover, in another configuration of the medical stopcock according to another embodiment of the present invention, the plural branch-tubes is comprised of a pair of horizontal branch-tubes extending from both sides of the outer peripheral surface of the chamber part outward and the vertical branch-tube extending from the top side of the outer peripheral surface of the chamber part upward, and that the flow passages of the valve main body is comprised of the horizontal flow passages capable of allowing the pair of horizontal branch-tubes to communicate with one another or shut-off the communication and the vertical flow passage capable of allowing the horizontal flow passages and the vertical branch-tube to communicate with one another or shut-off the communication.

This allows the horizontal flow passages to communicate with the pair of horizontal branch-tubes by positioning the valve main body at a predetermined location in the horizontal direction in the chamber part and, while maintaining the condition, also allows all of the pair of horizontal branch-tubes and the vertical branch-tube to communicate with one another through the use of the flow passages of the valve main body by positioning the valve main body at a predetermined location in the vertical direction to allow the vertical passage to communicate with the vertical branch-tube. Thereby, 2 kinds of drug solutions and the likes can be supplied into a patient's body from the horizontal branch-tube and the vertical branch-tube. Moreover, in the condition thereof, one side of the pair of horizontal branch-tubes can be shut-off by rotationally moving the valve main body to one side in the horizontal direction, and the other side of the pair of horizontal branch-tubes can be shut-off by rotationally moving the valve main body to the other side in the horizontal direction. In addition, with the condition in which all of the pair of horizontal branch-tubes and the vertical branch-tube are made to communicate, the vertical branch-tube can be shut-off by rotationally moving the valve main body in the vertical direction.

Further, in a configuration of the medical stopcock according to an embodiment of the present invention, the guide hole is comprised of the horizontal guide hole extending in the horizontal direction and the vertical guide hole extending from the approximately center of the horizontal guide hole upward or downward, and the rod-shaped operating part can be moved along the horizontal guide hole to allow the pair of horizontal branch-tubes to communicate with one another or shut-off the communication, and that the rod-shaped operating part can be moved along the vertical guide hole to allow the horizontal flow passages and the vertical branch-tube to communicate with one another or shut-off the communication.

In this case, it can be configured in such a manner that when the rod-shaped operating part is positioned at a portion where the horizontal guide hole and the vertical guide hole are intersected with one another, all of the pair of horizontal branch-tubes can be communicated with the vertical branch-tube, and when the rod-shaped operating part is moved from the position thereof, the branch-tubes located in the direction of the movement thereof can be shut-off or communicated. This allows the communication and shut-off statuses of each of the branch-tubes to be identified according to the position of the rod-shaped operating part, thereby an operational error can be prevented.

In another configuration of the medical stopcock according to an embodiment of the present invention, the plural branch-tubes are comprised of the pair of horizontal branch-tubes extending from both sides of the outer peripheral surface of the chamber part outward and the vertical branch-tube extending from the top side of the outer peripheral surface of the chamber part upward, and that the flow passages of the valve main body is comprised of the horizontal flow passages capable of allowing the pair of horizontal branch-tubes to communicate with one another or shut-off the communication and the vertical flow passage allowing the horizontal flow passages to constantly communicate with the vertical branch-tube. In this case, the guide hole is comprised of the horizontal guide hole extending in the horizontal direction so as to be capable of allowing the pair of horizontal branch-tubes to communicate with one another or shut-off the communication by moving the rod-shaped operating part along the horizontal guide hole.

In this case, the vertical branch-tube may be attached to a rubber plug into which the male luer part of the syringe, the puncture needle and the likes can be inserted. This allows the pair of horizontal branch-tubes to communicate with one another or shut-off the communication by positioning the valve main body at a predetermined location in the horizontal direction in the chamber part, and as required, the other drug solutions and the likes can be supplied into the chamber part from the vertical branch-tube.

Further still, in another configuration of the medical stopcock according to yet another embodiment of the present invention, both side portions of the valve main body opposing respectively to the flow passages of the pair of horizontal branch-tubes in the horizontal flow passages are formed in such a manner that when the valve main body is rotated to one side in the horizontal direction by the predetermined angle from the condition that the horizontal flow passages of the valve main body are made to communicate with the flow passages of the pair of horizontal branch-tubes respectively, the communication condition between the horizontal flow passages and the flow passages of one side branch-tube of the pair of branch-tubes is maintained, and the communication between the horizontal flow passages and the flow passage of the other branch-tube of the pair of branch-tubes is shut-off, whereas when the valve main body is rotated to the other side in the horizontal direction by the predetermined angle, the communication condition between the horizontal flow passages and the flow passage of the other branch-tube is maintained and the communication between the horizontal flow passages and the flow passage of one of branch-tubes is shut-off.

In this case, the term "by the predetermined angle" means that for example, based on the premises that the entire openings of the flow passages of the pair of horizontal branch-tubes face opposing to the horizontal flow passages, when the horizontal flow passages and the pair of horizontal branch-tubes are made to communicate with one another, the movement length of the valve main body in the outer peripheral surface is made equal to or greater than the width of the flow passage of one of branch-tubes in order to shut-off the flow passage of one of branch-tubes, and the movement length of the valve main body in the outer peripheral surface is made equal to or greater than the width of the flow passage of the other branch-tube in order to shut-off the flow passage of the other branch-tube. Hence, where the width of the flow passage of one of branch-tubes is different form the width of the flow passage of the other branch-tube, the respective predetermined angles may also be different.

Moreover, in the event that the horizontal flow passages are comprised of a hole passing through the valve main body, both end opening side portions of the horizontal flow passages can be formed as holes with the dimension wider in the horizontal direction than that of the center side portion to allow the communications between the horizontal flow passages and the pair of horizontal branch-tubes to open or shut-off. In addition, in the event that the horizontal flow passages are comprised of grooves formed along the surface of the valve main body, when the horizontal flow passages are made to communicate with the pair of horizontal branch-tubes one another, each of the both end parts of the horizontal flow passages can be positioned at each of the openings of the pair of branch-tubes to allow the communications between the horizontal flow passages and the pair of horizontal branch-tubes to open or shut-off.

What is claimed:

1. A medical stopcock comprising:
a medical stopcock main body including:
a chamber part having an inner surface defining an open space part, the inner surface being formed spherically, the chamber part defining a guide hole therein extending from the inner surface to an outside, the guide hole including a horizontal guide hole extending along a horizontal axis and a vertical guide hole extending from an approximate center of the horizontal guide hole along a vertical axis; and
plural branch-tubes extending outwardly from the chamber part, the plural branch-tubes including a pair of horizontal branch-tubes extending in opposite directions along the horizontal axis and a vertical branch-tube extending along the vertical axis; and
a valve main body defining an approximately spherical shape installed in the chamber part; and
a rod-shaped operating part passing through the guide hole, the rod-shaped operating part being configured to move along the horizontal guide hole to selectively control fluid communication between the pair of horizontal branch-tubes, the horizontal guide hole configured to permit movement of the rod-shaped operating part therealong in a horizontal direction and to substantially prevent movement of the rod-shaped operating part therealong in a vertical direction, and the rod-shaped operating part being configured to move along the vertical guide hole to selectively control fluid communication between the vertical branch-tube and the horizontal branch-tubes, the vertical guide hole configured to permit movement of the rod-shaped operating part therealong in a vertical direction and to substantially prevent movement of the rod-shaped operating part therealong in a horizontal direction.

2. A medical stopcock according to claim 1, wherein the rod-shaped operating part is configured to move along the horizontal guide hole to allow or shut-off communication between the pair of horizontal branch-tubes, and the rod-shaped operating part is configured to move along the vertical guide hole to allow or shut-off communication between the vertical branch-tube and the horizontal branch-tubes.

3. A medical stopcock according to claim 1, wherein the valve main body includes horizontal and vertical flow passages,
the horizontal flow passages being configured to allow or shut-off communication between the pair of horizontal branch-tubes; and
the vertical flow passage being configured to allow or shut-off communication between the pair of horizontal branch-tubes and the vertical branch-tube.

4. A medical stopcock according to claim 3, wherein the horizontal flow passages of the valve main body are configured to communicate with the pair of horizontal branch-tubes in a manner such that when the valve main body is rotated to a first side along the horizontal axis by a predetermined angle, the communication between the horizontal flow passages and a first horizontal branch-tube of the pair of horizontal branch-tubes is maintained, but the communication between the horizontal flow passages and a second horizontal branch-tube of the pair of branch tubes is shut-off, whereas when the valve main body is rotated to a second side along the horizontal axis by the predetermined angle, the communication between the horizontal flow passages and the second branch-tube is maintained, but the communication between the horizontal flow passages and the first branch-tube is shut-off.

5. A medical stopcock comprising:
a medical stopcock main body including:
a chamber part having an inner surface defining an open space, the inner surface being formed approximately spherically, the chamber part defining a guide hole therein extending from the inner surface to an outside, the guide hole including a horizontal guide hole extending along a horizontal axis and a vertical guide hole extending from the horizontal guide hole along a vertical axis; and plural branch-tubes extending outwardly from the chamber part, the plural branch-tubes including a pair of horizontal branch-tubes extending in opposite directions along the horizontal axis and a vertical branch-tube extending along the vertical axis, and a valve body including:

a valve main body defining an approximately spherical shape installed in the chamber part; and a rod-shaped operating part passing through the guide hole, the rod-shaped operating part being configured to move along the horizontal guide hole to selectively control fluid communication between the pair of horizontal branch-tubes, wherein substantial change in a degree of fluid communication through the vertical branch-tube is prevented during movement of the rod-shaped operating part along the horizontal guide hole, and the rod-shaped operating part being configured to move along the vertical guide hole to selectively control communication between the vertical branch-tube and the horizontal branch-tubes, wherein substantial change in a degree of fluid communication between the pair of horizontal branch-tubes is prevented during movement of the rod-shaped operating part along the vertical guide hole.

6. A medical stopcock according to claim 5, wherein the rod-shaped operating part is configured to move along the horizontal guide hole to allow or shut-off communication between the pair of horizontal branch-tubes.

7. A medical stopcock according to claim 5, wherein the rod-shaped operating part is configured to move along the vertical guide hole to allow or shut-off communication between the vertical branch-tube and the horizontal branch-tubes.

* * * * *